United States Patent
Cole et al.

(10) Patent No.: US 8,123,748 B2
(45) Date of Patent: Feb. 28, 2012

(54) INTRAMEDULLARY CANAL DIAMETER REDUCER

(75) Inventors: J. Dean Cole, Orlando, FL (US); Carl A. Knobloch, Oviedo, FL (US)

(73) Assignees: J. Dean Cole, Orland, FL (US); Carl A. Knobloch, Oviedo, FL (US)

( * ) Notice: Subject to any disclaimer, the term of this patent is extended or adjusted under 35 U.S.C. 154(b) by 830 days.

(21) Appl. No.: 12/173,749

(22) Filed: Jul. 15, 2008

(65) Prior Publication Data

US 2009/0005781 A1 Jan. 1, 2009

Related U.S. Application Data

(62) Division of application No. 10/362,664, filed as application No. PCT/US01/26253 on Aug. 22, 2001, now abandoned.

(60) Provisional application No. 60/226,865, filed on Aug. 22, 2000.

(51) Int. Cl.
*A61F 2/30* (2006.01)
(52) U.S. Cl. ............................................. 606/66; 606/62
(58) Field of Classification Search .............. 606/62–68, 606/95, 103, 104, 79, 82, 84, 86 R, 87–89; 623/20.32, 20.34–20.36, 22.4–22.42, 23.14, 623/23.15, 23.21–23.27, 23.46, 23.48, 23.52
See application file for complete search history.

(56) References Cited

U.S. PATENT DOCUMENTS

| | | | |
|---|---|---|---|
| 3,709,218 A | 1/1973 | Halloran | |
| 4,523,587 A * | 6/1985 | Frey | 606/86 R |
| 4,753,657 A * | 6/1988 | Lee et al. | 623/16.11 |
| 4,776,330 A * | 10/1988 | Chapman et al. | 606/64 |
| 4,838,252 A | 6/1989 | Klaue | |
| 5,002,544 A | 3/1991 | Klaue et al. | |
| 5,057,110 A | 10/1991 | Kranz et al. | |
| 5,062,843 A * | 11/1991 | Mahony, III | 606/232 |
| 5,078,746 A | 1/1992 | Garner | |
| 5,300,074 A | 4/1994 | Frigg | |
| 5,385,566 A | 1/1995 | Ullmark | |
| 5,425,768 A | 6/1995 | Carpenter et al. | |
| 5,549,612 A | 8/1996 | Yapp et al. | |
| 5,618,286 A | 4/1997 | Brinker | |
| 5,658,351 A | 8/1997 | Dudasik et al. | |
| 5,665,121 A | 9/1997 | Gie et al. | |
| 5,674,222 A | 10/1997 | Berger et al. | |
| 5,733,287 A | 3/1998 | Tepic et al. | |
| 5,788,704 A | 8/1998 | Timperley | |
| 5,876,455 A * | 3/1999 | Harwin | 128/898 |
| 6,368,326 B1 * | 4/2002 | Dakin et al. | 606/103 |
| 6,383,186 B1 | 5/2002 | Michelson | |
| 6,440,131 B1 | 8/2002 | Haidukewych | |
| 6,454,810 B1 | 9/2002 | Lob | |
| 6,623,486 B1 | 9/2003 | Weaver et al. | |
| 2001/0020187 A1 | 9/2001 | Guettinger et al. | |
| 2003/0004515 A1 | 1/2003 | Curtis et al. | |

\* cited by examiner

*Primary Examiner* — Eduardo C Robert
*Assistant Examiner* — Lynnsy Schneider
(74) *Attorney, Agent, or Firm* — Haynes and Boone, LLP

(57) ABSTRACT

A canal diameter reducer is placed within the intramedullary canal alongside an intramedullary rod to stabilize the intramedullary rod and prevent toggling and/or misalignment due to shear. The canal reducer is an elongated block which may be guided into position by a guide wire and may be held in position during insertion of the rod by a suture extending through hole 31. The reducer is inserted through an entry opening formed in the end of the fractured bone. The canal reducer may be fabricated from allograft bone or xenograft bone.

15 Claims, 3 Drawing Sheets

INTRAMEDULLARY CANAL DIAMETER REDUCER

CROSS-REFERENCE TO RELATED APPLICATION

The present application is a divisional of and claims priority to U.S. Ser. No. 10/362,664, having a 371(c) date of Sept. 22, 2003, entitled "Intramedullary Canal Diameter Reducer," which is a 371 application of International PCT/US01/26253, filed Aug. 22, 2001, which claims priority to provisional application No. 60/226,865 filed Aug. 22, 2000, each of which is incorporated by reference in its entirety.

BACKGROUND OF THE INVENTION

The present invention is directed to techniques and apparatus for reducing the toggle and/or misalignment of a fracture fixed with an intramedullary device as it is loaded. More specifically, but not exclusively, the present invention relates generally to a bioresorable intramedullary canal diameter reducer adapted to be placed within a specific point within the intramedullary canal. While the present invention was developed for reducing the intramedullary canal diameter at a specific point, certain applications may be in other areas.

With reference to FIG. 1, there is illustrated an example of a fracture repair wherein the diameter of a portion of the intramedullary canal is greater than the largest intramedullary rod or nail that can fit within the bone. As can be observed in FIG. 1, the diameter of the canal can vary over it's length and as a result of this difference in diameter the fracture fragments can "toggle" or become misaligned due to "shear" as the fracture is loaded.

One embodiment of the present invention might include a canal diameter reducer adapted to be placed within an intramedullary canal comprising a block of material having a shape, size and dimensions appropriate for being located within the intramedullary canal alongside an intramedullary member. The term intramedullary member is used herein to include intramedullary rods and intramedullary nails. The block stabilizes the intramedullary member and prevents toggling and/or misalignment due to shear.

Another embodiment of the invention is a canal diameter reducer adapted to be placed within an intramedullary canal and involving an elongated block having a concave inner surface extending longitudinally of the block. The block is adapted to be placed in the canal between an intramedullary member and the wall of the canal to prevent toggling and misalignment due to shear. The block is adapted to contact the intramedullary member with the concave inner surface of the block.

Still another embodiment of the invention involves a canal diameter reducer including a block having a convex outer surface which is provided with a series of projections for engagement with the bone to prevent movement relative to the bone. The block is adapted to be placed in the intramedullary canal between an intramedullary member and the wall of the canal with the series of projections in engagement with the wall of the canal. The block is adapted to engage the intramedullary member to prevent toggling and misalignment due to shear.

Still a further embodiment of the invention is a canal diameter reducer having tapered ends and a longitudinally extending aperture sized for reception of a guide wire. The block also has at least one hole therethrough for attachment of a suture. The block is adapted to be placed in the intramedullary canal between the intramedullary member and the wall of the canal to prevent toggling and misalignment due to shear.

Still a further embodiment of the invention is a canal diameter reducer having tapered ends and a concave inner surface extending longitudinally of the block. The block also has a convex outer surface. The tapered ends extend from the convex outer surface to the concave inner surface and taper in such a manner as to cause the outer surface to extend longitudinally a greater distance than the inner surface. The block is adapted to be placed in the intramedullary canal between an intramedullary member and the wall of the canal to prevent toggling and misalignment due to shear. The block contacts the intramedullary member with the concave inner surface.

Still another embodiment of the invention is a canal diameter reducer adapted to be placed within an intramedullary canal comprising an elongated block having a concave inner surface extending longitudinally of the block. The block has a convex outer surface which is provided with a series of projections for engagement with the bone to prevent movement relative to the bone. The block has tapered ends which extend from the convex outer surface to the concave inner surface and taper in such a manner as to cause the outer surface to extend longitudinally a greater distance than the inner surface. The block has a longitudinally extending aperture sized for reception of a guide wire and also has at least one hole therethrough for attachment of a suture. The block is adapted to be placed in the intramedullary canal with the concave inner surface in contact with an intramedullary member to prevent toggling and/or misalignment due to shear.

Still another embodiment of the invention is a process for reducing the toggle and misalignment of a fracture fixed with an intramedullary member. The process comprises forming an entry opening in the fractured bone in the end of the bone leading into the intramedullary canal. A further step is inserting a block through the entry opening into the intramedullary canal to reduce the diameter of the intramedullary canal. Finally an intramedullary member is inserted through the opening into the intramedullary canal to a position alongside the block.

One object of the present invention is to provide a unique intramedullary canal diameter reducer.

Further, forms, objects, features, aspects, benefits, advantages and embodiments of the present invention shall become apparent from the description and drawings provided herewith.

DESCRIPTION OF THE PREFERRED EMBODIMENTS

Figure 1:
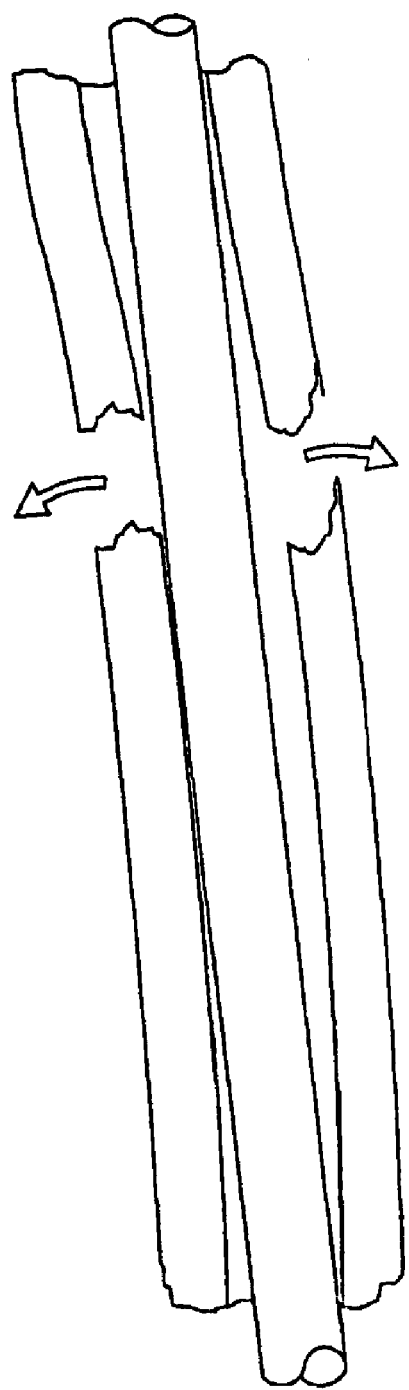
FIG. 1 is an illustrative cross sectional view of a intramedullary rod within a fracture repair that is manifesting a toggle type deficiency.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
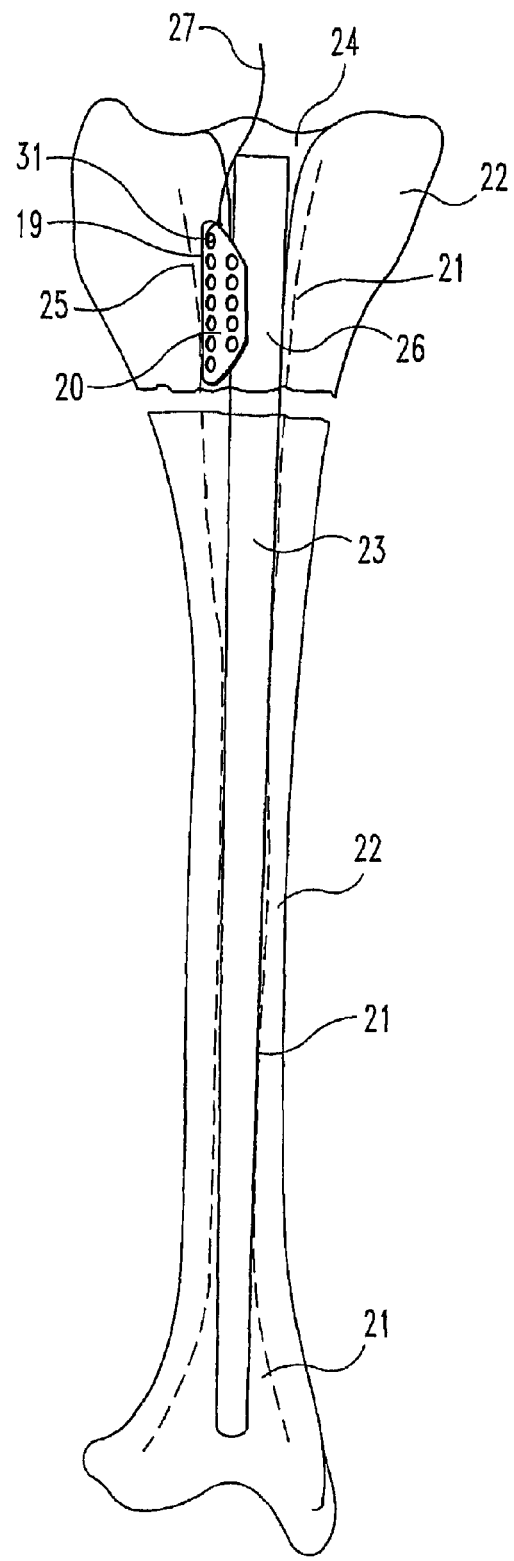
FIG. 2 is an illustrative view of one embodiment of the present invention intramedullary canal diameter reducer positioned within a fracture repair.
Figure 3:
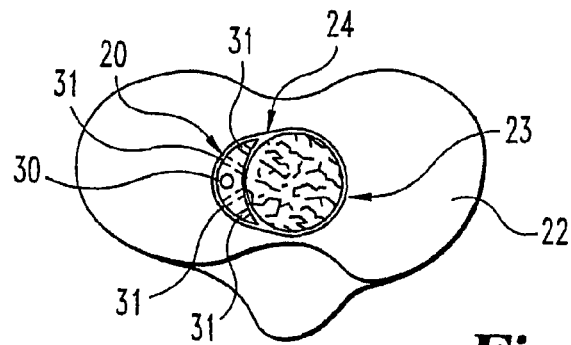
FIG. 3 is an illustrative end view of the intramedullary canal diameter reducer of FIG. 2.

With reference to FIG. 2, there is illustrated one embodiment of the intramedullary canal reducer 20 which is a body or block 19 positioned within the intramedullary canal 21 of the tibia 22. As illustrated in FIG. 2, the intramedullary canal diameter varies within the long bone and is typically widest at the proximal and distal ends and narrowest at the ishmus. The intramedullary rod 23 is introduced within the tibia 22 through an entry opening 24 formed in the end of the tibia. The canal reducer 20 is positioned between the wall 25 of the bone defining a portion of the intramedullary canal 21 and the outer surface 26 of the rod 23. The present invention will be described in terms of the tibia, however it is applicable to other bones including but not limited to repair of fractures of the femur and humerus. Further, the term intramedullary rod will be utilized to describe the present invention, however the present invention is equally applicable for use with intramedullary nails.

The intramedullary canal reducer 20 is utilized to locally reduce the diameter of the intramedullary canal and fill the gap between the intramedullary canal wall and the outer surface 26 of the rod 23. This localized filling of the gap acts to stabilize the rod 23 within the intramedullary canal 21 and minimize or prevent "toggling" and/or misalignment due to shear. The term diameter as utilized herein refers not only to the technical geometric term but also to the non-technical usage referring to an approximation of the width of an opening. In installing the canal reducer 20 the entry opening 24 is formed in the end of the bone and the canal reducer 20 is introduced through the entry opening prior to the insertion of the intramedullary rod 23. Further, in one embodiment the canal reducer 20 has at least one suture 27 coupled thereto and that extends out of the entry hole 24 to facilitate removal of the reducer if necessary and to be used to hold the canal reducer 20 in position during insertion of the intramedullary rod 23. The introduction of the intramedullary rod 23 will tend to push the canal reducer 20 down the intramedullary canal 21 unless the reducer is held in place. The present invention is not limited to the use of a suture 27 as the holding mechanism and contemplates other structures and quantities to accomplish this task. Further, in another embodiment of the present invention the canal reducer 20 does not include the suture 27 or other holding mechanisms.

Figure 4:
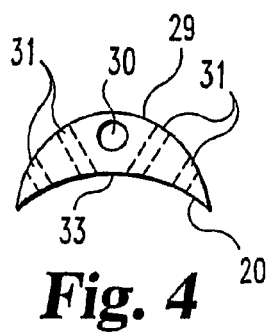
FIG. 4 is an enlarged illustrative end view of the intramedullary canal diameter reducer of FIG. 2 removed from the surgical location.
Figure 4A:
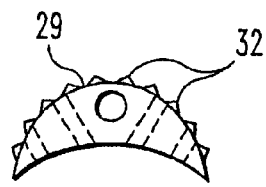
FIG. 4A is a view similar to FIG. 4 of an alternative embodiment of the invention.
Figure 5:
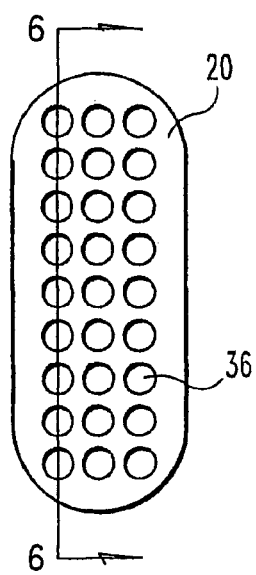
FIG. 5 is an illustrative front view of the intramedullary canal diameter reducer of FIG. 4.
Figure 6:
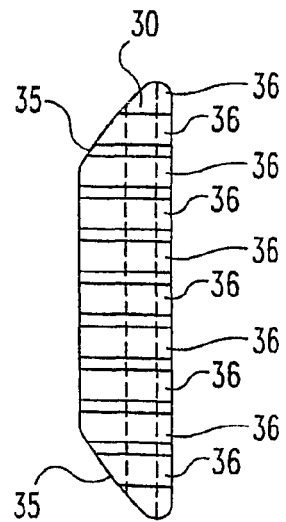
FIG. 6 is an illustrative sectional view of the intramedullary canal diameter reducer of FIG. 4 taken along the line 6-6 of FIG. 5.

With reference to FIGS. 3-6 the intramedullary canal reducer 20 will be described in greater detail. The canal reducer 20 includes at least one hole 31 for attaching the suture 27 to the body of the reducer. In the preferred embodiment there are four suture attachment holes 31 formed in the body 19 of the reducer 20. Further, the canal reducer includes an aperture 30 extending through the length of the body and adapted to receive a guide wire therein. With reference to FIG. 6, the aperture 30 is shown in phantom lines. The guide wire is utilized to help guide the canal reducer 20 into position and a K-wire may be utilized to temporarily hold the reducer in position. In another form of the present invention the surface of the reducer that is designed to be disposed adjacent to the bone has a surface treatment to minimize or prevent movement of reducer and temporarily hold it in position. As an example, as shown in FIG. 4A the surface 29 may be provided with a series of projections 32 for engagement with the bone to prevent movement relative to the bone. An alternate embodiment of the present invention does not include the aperture 30.

The reducer block 19 is shaped, sized and dimensioned appropriately to be located within the intramedullary canal alongside the intramedullary rod 23 with the concave elongated inner surface 33 of the reducer in contact with the surface 26 of the rod. The outer surface 29 of the body is convex so as to better fit against and engage the wall 25 of the bone of the intramedullary canal. The tapered ends 35 of the body 19 extend from the convex outer surface 29 to the concave inner surface and taper in such a manner as to cause the outer surface to extend longitudinally a greater distance than the inner surface 29. The tapered ends facilitate inserting the reducer through the entry opening 24.

In one embodiment the canal reducer 20 includes geometric features such as the tapered ends 35 to facilitate introduction of the intramedullary rod adjacent the reducer (already in position). The canal reducer is preferably formed of a bioresorbable material having a plurality of hole/pores 36 formed therein. The number and size of the holes/pores 36 and the material selection can be varied to alter the rate of resorbation. The suture holes 31 are not shown in FIGS. 5 and 6. However, alternatively the holes 36 can serve as suture holes. One type of material that could be used to form the canal reducer 20 is referred to as Bioresorbable PLLA and is described in U.S. Pat. No. 5,919,234, which is incorporated herein by reference. However, other types of material both bioresorbable and otherwise are contemplated herein. The canal reducer 20 may be solid, fabricated from sheet material or extruded. Also it may be shaped or formed in the operating room or it may be shaped or formed prior to the operation. Further it may be fabricated from allograft bone or xenograft bone. Further, a variety of sizes and geometric shapes are contemplated herein and the present invention is not intended to be limited to only one geometric shape as other geometric shapes are contemplated herein.

While the invention has been illustrated and described in detail in the drawings and the foregoing description, the same is to be considered as illustrative and not restrictive in character, it being understood that only the preferred embodiment has been shown and described and that all changes, equivalents, and modifications that come within the spirit of the invention defined by the following claims are desired to be protected. The term intramedullary member is used in the claims to include intramedullary rods and intramedullary nails.

What is claimed:

1. A process for reducing the toggle and/or misalignment of a fracture fixed with an intramedullary member which comprises forming an entry opening in the fractured bone in an end of the bone leading into the intramedullary canal, inserting a block through the entry opening into the intramedullary canal, positioning the block adjacent a proximal end of the intramedullary canal to reduce the diameter of the intramedullary canal adjacent the proximal end, and inserting an intramedullary member through the entry opening into the intramedullary canal to a position alongside said block such that the block extends around only a portion of a circumference of an outer surface of the intramedullary member, wherein the block is held in position adjacent the proximal end of the intramedullary canal as the intramedullary member is inserted into the intramedullary canal, and wherein at least a portion of the intramedullary member extends distally beyond the block towards a distal end of the intramedullary canal after insertion into the intramedullary canal.

2. The process of claim 1 additionally comprising providing said block with an aperture and guiding said block into the intramedullary canal by means of a guide wire extending through said aperture.

3. The process of claim 1 wherein the block is a canal diameter reducer comprising a block of material having a shape, size and dimension appropriate for being located within the intramedullary canal alongside an intramedullary member, said block stabilizing the intramedullary member and preventing toggling and/or misalignment due to shear.

4. The process of claim 1 wherein the block is a canal diameter reducer comprising an elongated block having a concave inner surface extending longitudinally of said block, said block being adapted to be placed in the intramedullary canal between an intramedullary member and the wall of the canal to prevent toggling and misalignment due to shear, said block being adapted to contact said intramedullary member with said concave inner surface.

5. The process of claim 1 wherein the block is a canal diameter reducer comprising an elongated bock having tapered ends and a concave inner surface extending longitudinally of said block, said block having a convex outer surface, said tapered ends extending from said convex outer surface to said concave inner surface and tapering in such a manner as to cause the outer surface to extend longitudinally a greater distance than said inner surface, said block being adapted to be placed in the intramedullary canal between an intramedullary member and the wall of the canal to prevent toggling and misalignment due to shear, said block being adapted to contact said intramedullary member with said concave inner surface.

6. The process of claim 1, wherein the block is held in position adjacent the proximal end of the intramedullary canal by a suture as the intramedullary mcmber is inserted into the intramedullary canal.

7. The process of claim 6, wherein the suture extends through an opening in the block, the opening extending in a direction transverse to a longitudinal axis of the block.

8. The process of claim 7, wherein the block is inserted over a guidewire.

9. The process of claim 8, wherein the guidewire extends through an aperture extending through the block along the longitudinal axis of the block.

10. The process of claim 1, wherein the intramedullary canal is an intramedullary canal of a tibia.

11. The process of claim 10, wherein the block has a concave inner surface configured to contact the intramedullary member, a convex outer surface configured to contact a wall of bone defining the intramedullary canal of the tibia, and tapered ends that extend from the convex outer surface to the concave inner surface such that the convex outer surface has a length along the longitudinal axis that is greater than a length of the concave inner surface along the longitudinal axis.

12. The process of claim 1, wherein the block is held in position adjacent the proximal end of the intramedullary canal by engagement of an outer surface of the block with a wall of hone defining the intramedullary canal as the intramedullary member is inserted into the intramedullary canal.

13. The process of claim 12, wherein the outer surface of the block includes a series of projections for engagement with the wall of hone to prevent movement relative to the wall of bone during insertion of the intramedullary member.

14. A process for reducing the toggle and/or misalignment of a fracture fixed with an intramedullary member which comprises forming an entry opening in the fractured bone in an end of the bone leading into the intramedullar canal insertin a block through the entry opening, into the intramedullary canal to reduce the diameter of the intramedullary canal, and inserting an intramedullary member through the entry opening into the intramedullary canal to a position alongside said block such that a first proximal portion of an outer surface of the intramedullary member is in contact with the block and a second proximal portion of the outer surface opposite the first proximal portion is spaced from the block; and attaching a suture to the block, holding the suture stationary relative to the bone so as to hold the block in place and prevent the block from being inserted further into the intramedullary canal when the intramedullary member is inserted into the intramedullary canal.

15. A process for reducing the toggle and/or misalignment of a fracture fixed with an intramedullary member which comprises forming an entry opening in an fractured bone in an end of the bone leading into the intramedullary canal, inserting a block through the entry opening into the intramedullary canal to reduce the diameter of the intramedullary canal, and inserting an intramedullary member through the entry opening into the intramedullary canal to a position alongside said block such that the block extends around only a portion of a circumference of an outer surface of the intramedullary member, wherein the block is a canal diameter reducer comprising an elongated block having a concave inner surface extending longitudinally of said block, said block having a convex outer surface which is provided with a series of projections for engagement with bone to prevent movement relative to bone, said block having tapered ends which extend from said convex outer surface to said concave inner surface and taper in such a manner as to cause the outer surface to extend longitudinally a greater distance than said inner surface, said block having a longitudinally extending aperture sized for reception of a guide wire, said block also having at least one hole therethrough for attachment of a suture, said block being adapted to be placed in the intramedullary canal with said concave inner surface in contact with an intramedullary member to prevent toggling and/or misalignment due to shear.

* * * * *